United States Patent [19]

Bozzelli et al.

[11] 4,228,096
[45] Oct. 14, 1980

[54] METHOD OF PREPARING QUATERNARY AMMONIUM SALTS FROM VARIOUS MORPHOLINONES

[75] Inventors: John W. Bozzelli; Nancy J. Morris, both of Midland, Mich.

[73] Assignee: The Dow Chemical Company, Midland, Mich.

[21] Appl. No.: 30,583

[22] Filed: Apr. 16, 1979

Related U.S. Application Data

[62] Division of Ser. No. 908,191, May 22, 1978, abandoned.

[51] Int. Cl.$^2$ ............... C07C 141/04; C07C 103/183; C07C 103/28
[52] U.S. Cl. ..................... 260/459 A; 260/501.15; 260/559 A; 260/561 A; 260/562 N; 424/303; 424/320; 424/324
[58] Field of Search .......... 260/459 A, 559 A, 561 A, 260/562 N, 501.15

[56] References Cited

U.S. PATENT DOCUMENTS

| | | | |
|---|---|---|---|
| 2,139,190 | 12/1938 | Iselin et al. ................. | 260/561 A |
| 2,168,253 | 8/1939 | Balle et al. ................. | 260/459 A |
| 2,317,999 | 5/1943 | Leuchs ....................... | 260/561 A |
| 3,042,720 | 7/1962 | Paabo ........................ | 260/562 N |
| 3,073,822 | 1/1963 | Schultz et al. ............. | 544/173 |
| 3,635,974 | 1/1972 | Freter et al. ............... | 260/559 A |
| 3,718,693 | 2/1973 | Samour et al. .............. | 260/561 A |
| 4,015,013 | 3/1977 | Passedouet et al. ......... | 260/459 A |

Primary Examiner—Nicky Chan

[57] ABSTRACT

Quaternary ammonium salts of the formula

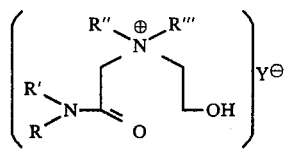

where R, R', R" and R''' are typically individually alkyl or inertly-substituted alkyl radicals and Y$^\ominus$ is a neutralizing anion, are facilely prepared by amidating the carbonyl carbon and subsequently quaternizing the ring nitrogen of an N-alkyl morpholinone. These quaternary ammonium salts demonstrate biological, antistatic and surfactant activity.

9 Claims, No Drawings

METHOD OF PREPARING QUATERNARY AMMONIUM SALTS FROM VARIOUS MORPHOLINONES

CROSS REFERENCE TO RELATED APPLICATION

This is a division of application Ser. No. 908,191, filed May 22, 1978, now abandoned.

BACKGROUND OF THE INVENTION

1. Field of the Invention

This invention relates to novel quaternary ammonium salts, a process for their preparation and their use as antimicrobials, antistatic agents and surfactants.

2. Description of the Prior Art

Quaternary ammonium compounds as a class have long been known in the art and vary in size and complexity from tetramethylammonium salts to polymeric compounds. These salts have a wide variety of utility which includes surfactants, germicides, thickening and antistatic agents, etc.

SUMMARY OF THE INVENTION

This invention provides a new subclass of quaternary ammonium salts. These salts demonstrate biological, antistatic and surfactant activity and are of the formula

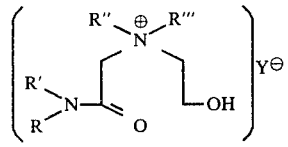
(I)

where

R, R' and R''' are individually hydrogen, an aliphatic, alicyclic, aryl or an inertly-substituted aliphatic, alicyclic or aryl radical;

R'' is a $C_1$–$C_5$ alkyl radical; and $Y^{\ominus}$ is a neutralizing anion.

"Individually" here means that R, R' and R''' can be the same or different, e.g., R, R' and R''' can be simultaneously methyl or R can be methyl while at the same time R' is ethyl and R''' is propyl. The aliphatic and alicyclic radicals of R, R' and R''' are typically of 1 to about 30 carbon atoms, preferably of 8 to about 20 carbon atoms, and the aryl radical is typically and preferably phenyl. The quaternary ammonium salts of this invention are facilely prepared by amidating the carbonyl carbon, and subsequently quaternizing the ring nitrogen, of an N-alkyl morpholinone.

DETAILED DESCRIPTION OF THE INVENTION

N-alkyl morpholinones (II) are known compounds and can be prepared by either reacting 2-p-dioxanone and a primary amine (U.S. Pat. No. 3,092,630) or by dehydrogenation of an N-alkyl dialkanolamine (U.S. Pat. No. 3,073,822).

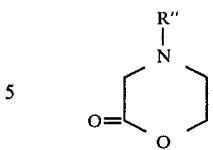
(II)

Here, as elsewhere herein, R'' is preferably methyl. Moreover, the ring carbons (except for the carbonyl carbon) of II and the corresponding carbons of the other formulae herein can bear a $C_1$–$C_4$ alkyl radical. Preferably, these carbons are unsubstituted except for the hydroxyl radical of the terminal carbon of I and like noncyclic formulae.

The preparation of the quaternary ammonium salts of this invention is a two-step method, one step of which is the amidation of the carbonyl carbon of a morpholinone and the other step of which is the quaternization of the ring nitrogen of the same morpholinone. The order in which these steps are practiced is not critical to this invention but preferably the first step is the amidation of the carbonyl carbon of a morpholinone according to the following equation

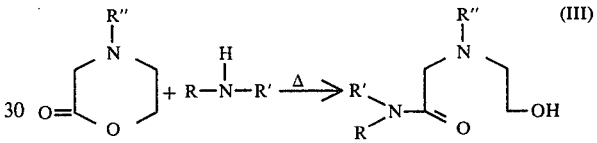
(III)

$\Delta$ here means heat. The amidating agent,

(IV)

can be any primary or secondary amine wherein R and R' are as previously defined. The aryl radicals of R and R' include: phenyl, biphenyl, naphthyl, anthracyl, phenanthracyl, etc. with phenyl the preferred aryl radical. Preferably, the aminating agent is a primary amine where either R or R' is an aliphatic, alicyclic or an inertly-substituted aliphatic or alicyclic radical of 8 to about 20 carbon atoms. "Inertly-substituted" means that the aliphatic, alicyclic and aryl radicals can bear one or more substituents that are essentially nonreactive with the products or the reagents of the processes of III and V. Illustrative inert-substituents include: ether oxygen, carbonyl, other aliphatic, alicyclic or aryl radicals, aralkyl, amino, imino, cyano, etc. Most preferably, the amidating agent is a primary amine where either R or R' is an unsubstituted (i.e., without inert-substituents) aliphatic, most preferably alkyl, radical of 8 to about 20 carbon atoms. Representative amidating agents include:

ammonia, methylamine, ethylamine, propylamine, isopropylamine, octylamine, nonylamine, undecylamine, dodecylamine, octadecylamine, eicosanylamine, dimethylamine, diethylamine, dipropylamine, dioctylamine, didodecylamine, methylethylamine, ethylbutylamine, octylnonylamine, octynylamine, oleylamine, benzylamine, phenethylamine, cyclopentylamine, cyclohexylamine, aniline, diphenylamine, etc.

The process of III is typically conducted under an inert atmosphere, such as nitrogen, and at a temperature of about 50° C. to about 250° C., and preferably of about 150° C. to about 200° C. The maximum temperature here used is determined generally by the boiling point of the amidating agent, the maximum temperature generally not exceeding the boiling point of the amidating agent. The minimum temperature here used is sufficient to maintain liquid all the reagents of process III.

Process III can be conducted at reduced, atmospheric or superatmospheric pressure although autogenous, typically atmospheric, pressure is preferred.

A suitable solvent, such as tetrahydrofuran, can be used if desired but process III is preferably conducted neat.

Preferably, the second step in the preparation of the quaternary ammonium salts of this invention is the quaterization of the product of process III, i.e.,

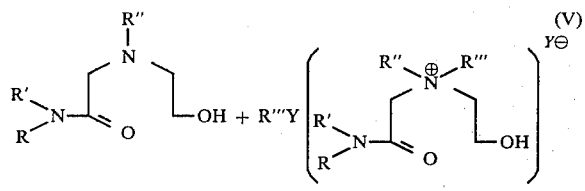

The quaternizing agent, $$R'''Y \quad \quad (VI)$$

can be any compound that will both quaternize the original ring nitrogen and provide a neutralizing anion $(Y^\ominus)$ after the quaternization. $R'''$ is as previously defined. The aryl radicals of $R'''$ are as defined for R and R' and the preferred aryl radical is phenyl. The aliphatic, alicyclic and aryl radicals of $R'''$ can bear the same kind and number of inert substituents as the like radicals of R and R'. Preferably, $R'''$ is an aliphatic, alicyclic or an inertly-substituted aliphatic or alicyclic radical of 8 to about 20 carbon atoms.

$Y^\ominus$ can be any suitable anion, such as halogen anion, e.g., fluoride, chloride, bromide, etc.; alkyl sulfate, e.g., methylsulfate, ethylsulfate, etc.; bisulfate; an organic anion, e.g., tosylate, acetate, etc.; and the like. Aliphatic and inertly-substituted aliphatic halides and sulfates are the preferred quaternizing agents. Representative quaternizing agents include: dimethyl sulfate, 3-bromo-1,1-dichloropropene, 1,3-dichloropropene, α-bromo-4-nitrotoluene, octylbromide, benzylchloride, methylethyl sulfate, bromobenzene, iodobenzene, etc.

The process of V is conducted under an inert atmosphere, such as nitrogen, and is usually conducted at a temperature of about 25° C. to about 150° C. and preferably at a temperature between about 40° C. and 60° C. However, the process of V, unlike the process of III, is exothermic and thus generates its own heat. For reasons of convenience, the temperature of V is maintained within the stated broad range, preferably within the stated narrow range, and is readily controlled by monitoring the rate of addition of one reagent to another, preferably by monitoring the rate of addition of the quaternizing agent to the product of process III. Other control means, such as a cooling jacket, can also be used.

Like process III, process V can be conducted at any pressure but autogenous (usually atmospheric) pressure is preferred.

Process V can also be conducted either neat or in the presence of an inert solvent, but unlike process III, process V is preferably conducted in the presence of a solvent, preferably a polar solvent, such as tetrahydrofuran. Other suitable solvents include: hexane, cyclohexane, benzene, chloroform, carbon tetrachloride, etc.

Both steps of the process require stoichiometric amounts of the respective reagents but are preferably conducted in a slight excess of amidating agent and quaternizing agent, respectively. Typically, after completion of the first process step, the quaternizing agent can be added directly to the reaction product of process III without a prior separation or purification step.

The final product, i.e., the quaternary ammonium salt, is typically a colored, highly viscous liquid or waxy solid material, the color ranging from water-white to dark brown depending upon the quaternizing agent employed. The overall process is clean, efficient and facile. Product yield from each process step and from the overall process is essentially quantitative.

The quaternary ammonium salts of this invention are useful antimicrobials, antistatic agents and surfactants and are used in the same manner as known antimicrobials, antistatic agents and surfactants.

The following examples are illustrative embodiments of this invention. Unless indicated to the contrary, all parts and percentages are by weight.

SPECIFIC EMBODIMENTS

Example 1: Ethanaminium: N-(2-hydroxyethyl)N,N-dimethyl-2-oxo-(2-undecylamino), methylsulfate N-methyl-2-morpholinone (6.98 g) and n-undecylamine (11.44 g) were charged to a 3-neck, 50 ml flask equipped with a dropping funnel, water-cooled condenser and nitrogen bleed. The contents were gradually heated with constant agitation to about 180° C. and then maintained at about 180° C. for about an additional 2½ hours.

The reaction mixture was then allowed to cool to room temperature after which it was dissolved in tetrahydrofuran (about 20 ml). Dimethyl sulfate (7.65 g) was then added dropwise by the dropping funnel while monitoring the flask temperature. After approximately 2 minutes, a mild exotherm (about 25° C.) was observed. After the completion of the addition of the dimethyl sulfate, the reaction mixture was stirred for about an additional 2 hours. The final product was then washed with tetrahydrofuran, the tetrahydrofuran evaporated, the product dissolved in diethyl ether and subsequently the diethyl ether evaporated at a temperature of about 80° C. The final product was a slightly yellow, highly viscous liquid material recovered in essentially a quantitative yield and was identified by infrared, nuclear magnetic resonance and carbon, hydrogen and nitrogen elemental analysis.

EXAMPLES 2–9

The procedure of Example 1 was repeated except various amidating and quaternizing agents were substituted for the n-undecylamine and dimethyl sulfate, respectively. In each example, the yields of product exceeded 90 percent of theory. N-methyl-2-morpholinone was a starting reagent in each of the examples and the other starting reagents as well as respective products are reported in Table I.

TABLE I
NOVEL QUATERNARY AMMONIUM SALTS

| Ex. | Amidating Agent | Quaternizing Agent | Quaternary Ammonium Salt |
|---|---|---|---|
| 2 | $CH_3(CH_2)_7NH_2$<br>Octylamine | $(CH_3)_2SO_4$<br>Dimethyl sulfate | Ethanaminium: N-(2-hydroxyethyl)-N,N-dimethyl-2-(octylamino)-2-oxo-, methyl sulfate |
| 3 | $CH_3(CH_2)_8NH_2$<br>Nonylamine | $(CH_3)_2SO_4$<br>Dimethyl sulfate | Ethanaminium: N-(2-hydroxyethyl)-N,N-dimethyl-2-(nonylamino)-2-oxo-, methyl sulfate |
| 4 | $CH_3(CH_2)_{10}NH_2$<br>Undecylamine | $BrCH_2-CH=CCl_2$<br>3-Bromo-1,1-dichloropropene | 2-Propen-1-aminium: 3,3-Dichloro-N-(2-hydroxyethyl)-N-methyl-N-(2-oxo-2-(undecylamino)-ethyl)-, bromide |
| 5 | $(CH_3(CH_2)_{10}NH_2$<br>Undecylamine | $Cl-CH_2-CH=CH$<br>$\quad\quad\quad\quad\quad\;\;Cl$<br>1,3-Dichloropropene | 2-Propen-1-aminium: 3-chloro-N-(2-hydroxyethyl)-N-methyl-N-(2-oxo-2-(undecylamino)-ethyl)-, chloride |
| 6 | $CH_3(CH_2)_{12}NH_2$<br>Tridecylamine | $(CH_3)_2SO_4$<br>Dimethyl sulfate | Ethanaminium: N-(2-hydroxyethyl)-N,N-dimethyl-2-oxo-2-(tridecylamino)-, methyl sulfate |
| 7 | $CH_3(CH_2)_{10}NH_2$<br>Undecylamine | $BrCH_2-\text{C}_6H_4-NO_2$<br>α-Bromo-4-nitrotoluene | Benzenemethanaminium: N-(2-hydroxyethyl)-N-methyl-4-nitro-N-(2-oxo-2-(undecylamino)-ethyl)-, bromide |
| 8 | $CH_3(CH_2)_{17}NH_2$<br>Octadecylamine | $(CH_3)_2SO_4$<br>Dimethyl sulfate | Ethanaminium: N-(2-hydroxyethyl)-N,N-dimethyl-2-(octadecylamino)-2-oxo-, methyl sulfate |
| 9 | $CH_3(CH_2)_7CH=CH(CH_2)_8NH_2$<br>Oleylamine | $(CH_3)_2SO_4$<br>Dimethyl sulfate | Ethanaminium: N-(2-hydroxyethyl)-N,N-dimethyl-2-(oleylamino)-2-oxo, methyl sulfate |

EXAMPLES 10–17: Antimicrobial Activity

The products of Examples 1–8 were screened for antimicrobial activity by the following procedure. Each product was individually loaded onto a silica gel at a concentration of 500 ppm, a 0.05 g sample of each loaded silica gel was then individually mixed with molten media (20 ml) and subsequently poured into premarked individual Petri dishes. After the media had cooled and with sterile technique, each Petri dish was inoculated with a microorganism, dishes containing a product of Example 1, 3-8 with *staphylococcus aureus* and dishes containing the product of Example 2 with *trichophyton mentagrophytes*. After incubation at about 37° C. for 24 hours, each of the products had inhibited the normal growth of the microorganisms.

EXAMPLE 18: Antistatic Activity

The product of Example 9 was screened for antistatic activity by the following procedure. A 6½ pound load consisting of polyester and knit fabric swatches (2"×6" strips) were charged to a Maytag washer with settings at warm wash (50° C.), cold rinse (12° C.) and medium water level (14 gal.). The product of Example 9 (6 g) was charged to the warm wash water. After the wash cycle was completed, the load was transferred to a dryer and dried at approximately 70° C. The swatches were then put into a controlled room to equilibrate to temperature (70°-74° F.) and relative humidity (30-40 percent). A Pasco® Electrometer equipped with a Faraday Cage was calibrated. One of each type of swatch was then hand rubbed as consistently as possible and dropped into the cage for measurement. A control procedure (wash, dry and measurement) was also conducted. The results of both the control and the test procedure were Control: −748 V
Product of Example 9: −234 V Generally, a static measurement value between 0 and −300 volts is considered acceptable while a static measurement value in excess (farther from 0) of −700 volts is considered poor.

Although this invention has been described in considerable detail with respect to the above examples, such detail is for the purpose of illustration only and is not to be construed as a limitation upon the invention. Many variations can be had without departing from the spirit of the invention or the scope of the appended claims.

What is claimed is:

1. A method for preparing a compound of the formula

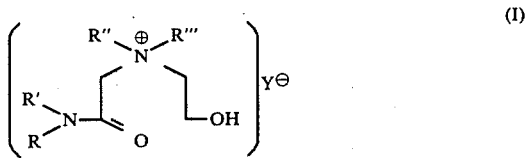

(I)

where
R, R' and R''' are individually hydrogen, an aliphatic, alicyclic, aryl or an inertly-substituted aliphatic, alicyclic or aryl radical;
R'' is a $C_1$–$C_5$ alkyl radical; and
$Y^\ominus$ is a neutralizing anion,
the method comprising:
(a) contacting at a temperature of about 50° C. to about 250° C. a morpholinone of the formula

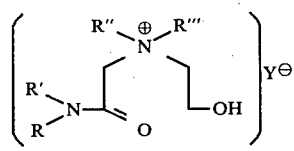

(II)

with an amidating agent of the formula

and
(b) contacting at a temperature of about 25° C. to about 150° C. the reaction product of (a) with a quaternizing agent of the formula R'''Y where R, R', R'', R''' and Y are as previously defined.

2. A method for preparing a compound of the formula

(I)

where
R, R' and R''' are individually hydrogen, an aliphatic, alicyclic, aryl or an inertly-substituted aliphatic, alicyclic or aryl radical;
R'' is a $C_1$–$C_5$ alkyl radical; and
$Y^\ominus$ is a neutralizing anion,
the method comprising:
(a) contacting at a temperature of about 25° C. to about 150° C. a morpholinone of the formula

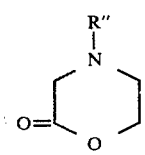

(II)

with a quaternizing agent of the formula R'''Y; and
(b) contacting at a temperature of about 50° C. to about 250° C. the reaction product of (a) with an amidating agent of the formula

where R, R', R'', R''' and Y are as previously defined.

3. The method of claim 1 or 2 where the aliphatic and alicyclic radicals of R, R' and R''' are of 1 to about 30 carbon atoms.

4. The method of claim 1 or 2 where the aryl radical of R, R' and R''' is phenyl.

5. The method of claim 1 or 2 where R and R' are individually hydrogen or an alkyl radical of 8 to about 20 carbon atoms.

6. The method of claim 5 where R''' is an aliphatic, alicyclic or an inertly-substituted aliphatic or alicyclic radical of 8 to about 20 carbon atoms.

7. The method of claim 6 where Y is methylsulfate, bisulfate or halogen.

8. The method of claim 1 or 2 where the amidating agent is undecyl-, octyl-, nonyl-, tridecyl-, octadecyl- or oleylamine.

9. The method of claim 8 where the quaternizing agent is dimethyl sulfate, 3-bromo-1,1-dichloropropene, 1,3-dichloropropene or α-bromo-4-nitrotoluene.

* * * * *